US012633051B1

(12) United States Patent
    Imanuel et al.

(10) Patent No.: US 12,633,051 B1
(45) Date of Patent: May 19, 2026

(54) SYSTEMS AND METHODS FOR DETERMINING TRANSDUCER LOCATIONS FOR DELIVERING TUMOR TREATING FIELDS USING A DISCRETIZED MODEL OF A SUBJECT

(71) Applicant: Novocure GmbH, Root (CH)

(72) Inventors: Ido Imanuel, Haifa (IL); Michal Holtzman Gazit, Haifa (IL); Reuven Ruby Shamir, Haifa (IL)

(73) Assignee: Novocure GmbH, Baar (CH)

( * ) Notice: Subject to any disclaimer, the term of this patent is extended or adjusted under 35 U.S.C. 154(b) by 312 days.

(21) Appl. No.: 18/510,130

(22) Filed: Nov. 15, 2023

Related U.S. Application Data

(60) Provisional application No. 63/426,488, filed on Nov. 18, 2022.

(51) Int. Cl.
    *G06T 17/00*      (2006.01)
    *A61B 6/03*       (2006.01)
    (Continued)

(52) U.S. Cl.
    CPC .............. *G06T 17/00* (2013.01); *A61B 6/032* (2013.01); *A61N 1/0476* (2013.01);
    (Continued)

(58) Field of Classification Search
    CPC .. A61B 6/032; A61N 1/0376; A61N 1/36002; G06T 7/0012; G06T 17/00; G06T 2207/10081; G06T 2210/41
    See application file for complete search history.

(56) References Cited

U.S. PATENT DOCUMENTS 5,119,816 A * 6/1992 Gevins ................. A61B 5/1077
                                                    600/386
7,565,205 B2   7/2009 Palti
        (Continued)

OTHER PUBLICATIONS

Korshoej et al. "Importance of electrode position for the distribution of tumor treating fields (TTFields) in a human brain. Identification of effective layouts through systematic analysis of array positions for multiple tumor locations." PLoS One 13.8 (2018): e0201957. (Year: 2018).*

(Continued)

*Primary Examiner* — Katrina R Fujita
(74) *Attorney, Agent, or Firm* — McCarter & English, LLP; Michael A. Sartori

(57)          ABSTRACT

A computer-implemented method for selecting at least one transducer location for delivering tumor treating fields to a subject, the method including: obtaining a three-dimensional model which includes voxels associated with image data of the subject; computing a discretization of the model to obtain a discretized model; computing boundary conditions for the discretized model; computing a matrix A is based on the discretized model and a vector b based on the boundary conditions for each respective transducer location; computing a vector φ using the matrix A and the vector b for each transducer location, wherein the vector φ is computed by computationally solving an equation Aφ=b, wherein each vector φ represents electrical potentials for the discretized model for each respective transducer location; and selecting one or more transducer locations for delivering tumor treating fields to the subject based on the vectors φ.

20 Claims, 4 Drawing Sheets

(51) Int. Cl.
*A61N 1/04* (2006.01)
*A61N 1/36* (2006.01)
*G06T 7/00* (2017.01)

(52) U.S. Cl.
CPC ........ *A61N 1/36002* (2017.08); *G06T 7/0012* (2013.01); *G06T 2207/10081* (2013.01); *G06T 2210/41* (2013.01)

(56) References Cited

U.S. PATENT DOCUMENTS

| | | | | |
|---|---|---|---|---|
| 12,115,381 | B2 * | 10/2024 | Urman | G16H 20/40 |
| 12,343,529 | B2 * | 7/2025 | Shamir | G06T 17/00 |
| 2005/0276616 | A1 * | 12/2005 | Sasaki | G03G 15/50 |
| | | | | 399/1 |
| 2009/0265128 | A1 * | 10/2009 | Markowitz | A61B 34/20 |
| | | | | 702/94 |
| 2012/0226200 | A1 * | 9/2012 | Wagner | A61N 1/36082 |
| | | | | 607/45 |
| 2017/0120041 | A1 * | 5/2017 | Wenger | A61B 5/055 |
| 2018/0160933 | A1 * | 6/2018 | Urman | G16H 50/50 |
| 2019/0308016 | A1 * | 10/2019 | Wenger | G01R 33/5607 |
| 2020/0023179 | A1 * | 1/2020 | Bomzon | G16H 30/40 |
| 2020/0146572 | A1 * | 5/2020 | Bar-Tal | G16H 20/40 |
| 2020/0146586 | A1 * | 5/2020 | Naveh | A61B 6/501 |
| 2020/0372705 | A1 * | 11/2020 | Hershkovich | G06T 19/00 |
| 2021/0060334 | A1 * | 3/2021 | Avraham | G16H 50/50 |
| 2021/0162228 | A1 * | 6/2021 | Urman | A61N 1/403 |
| 2021/0196207 | A1 * | 7/2021 | Shamir | G16H 50/20 |
| 2021/0196943 | A1 * | 7/2021 | Shamir | G16H 20/30 |
| 2021/0196967 | A1 * | 7/2021 | Carlson | A61N 1/36002 |
| 2021/0201572 | A1 * | 7/2021 | Bomzon | G06T 19/20 |
| 2021/0299439 | A1 * | 9/2021 | Shamir | G06T 7/0012 |
| 2022/0096829 | A1 * | 3/2022 | Farber | G16H 50/50 |
| 2022/0207425 | A1 * | 6/2022 | Nakae | G06F 17/16 |

OTHER PUBLICATIONS

Korshoej, Anders Rosendal. "Estimation of TTFields intensity and anisotropy with singular value decomposition: a new and comprehensive method for dosimetry of TTFields." Brain and human body modeling: Computational human modeling at EMBC 2018 (2019): 173-193. (Year: 2019).*

Korshoej et al. "Enhancing predicted efficacy of tumor treating fields therapy of glioblastoma using targeted surgical craniectomy: a computer modeling study." PLoS One 11.10 (2016): e0164051. (Year: 2016).*

Saturnino et al. "On the importance of electrode parameters for shaping electric field patterns generated by tDCS." Neuroimage 120 (2015): 25-35. (Year: 2015).*

Shamir et al. "A Method for Tumor Treating Fields Fast Estimation." International Workshop on Simulation and Synthesis in Medical Imaging. Cham: Springer International Publishing, 2020. (Year: 2020).*

Thielscher et al. "Field modeling for transcranial magnetic stimulation: A useful tool to understand the physiological effects of TMS?." 2015 37th annual international conference of the IEEE engineering in medicine and biology society (EMBC). IEEE, 2015. (Year: 2015).*

Wenger et al. "A review on tumor-treating fields (TTFields): clinical implications inferred from computational modeling." IEEE Reviews in Biomedical Engineering 11 (2018): 195-207. (Year: 2018).*

* cited by examiner

100

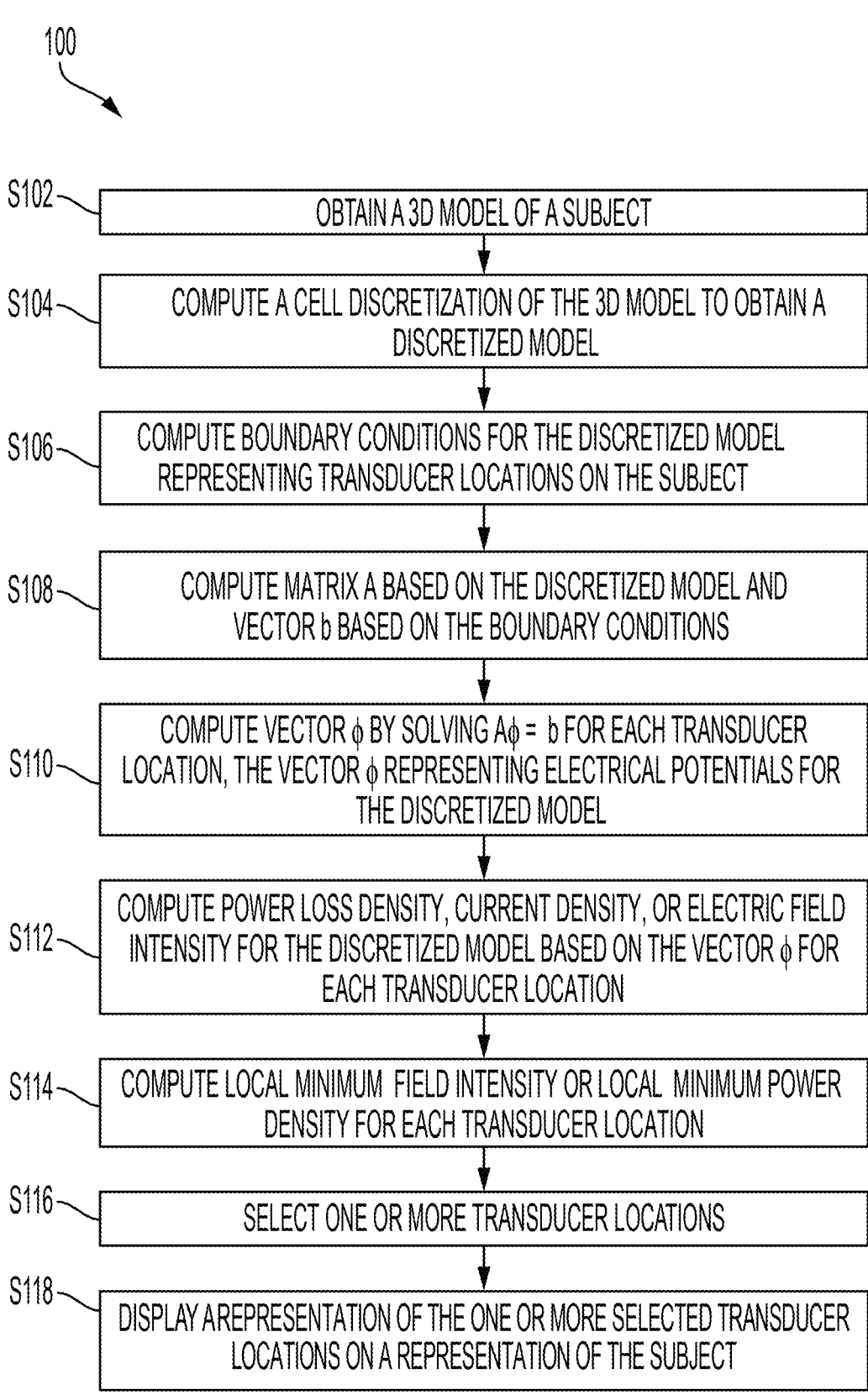

S102 — OBTAIN A 3D MODEL OF A SUBJECT

S104 — COMPUTE A CELL DISCRETIZATION OF THE 3D MODEL TO OBTAIN A DISCRETIZED MODEL

S106 — COMPUTE BOUNDARY CONDITIONS FOR THE DISCRETIZED MODEL REPRESENTING TRANSDUCER LOCATIONS ON THE SUBJECT

S108 — COMPUTE MATRIX A BASED ON THE DISCRETIZED MODEL AND VECTOR b BASED ON THE BOUNDARY CONDITIONS

S110 — COMPUTE VECTOR $\phi$ BY SOLVING $A\phi = b$ FOR EACH TRANSDUCER LOCATION, THE VECTOR $\phi$ REPRESENTING ELECTRICAL POTENTIALS FOR THE DISCRETIZED MODEL S112 — COMPUTE POWER LOSS DENSITY, CURRENT DENSITY, OR ELECTRIC FIELD INTENSITY FOR THE DISCRETIZED MODEL BASED ON THE VECTOR $\phi$ FOR EACH TRANSDUCER LOCATION S114 — COMPUTE LOCAL MINIMUM FIELD INTENSITY OR LOCAL MINIMUM POWER DENSITY FOR EACH TRANSDUCER LOCATION

S116 — SELECT ONE OR MORE TRANSDUCER LOCATIONS

S118 — DISPLAY A REPRESENTATION OF THE ONE OR MORE SELECTED TRANSDUCER LOCATIONS ON A REPRESENTATION OF THE SUBJECT

FIG. 1

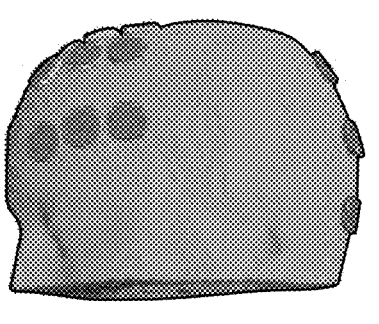
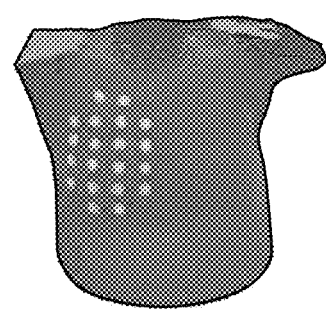
FIG. 4          FIG. 5
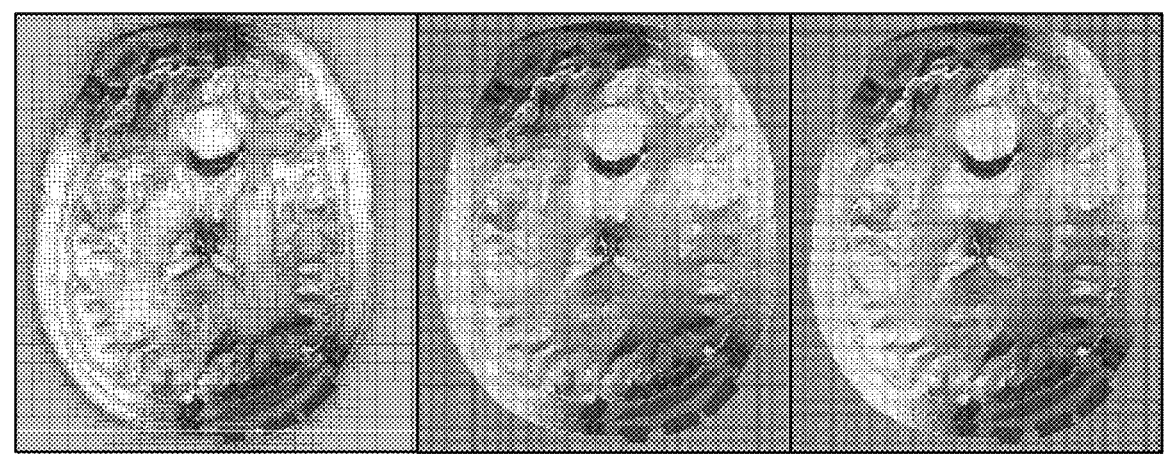
FIG. 6A          FIG. 6B          FIG. 6C
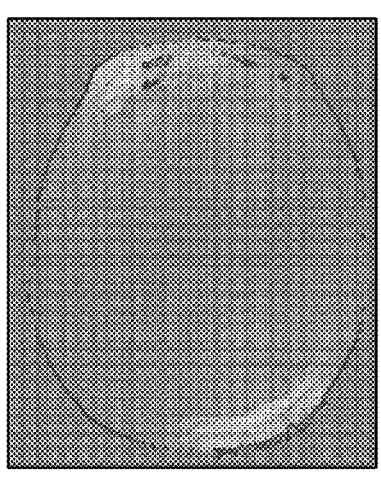
FIG. 6D          FIG. 6E

SYSTEMS AND METHODS FOR DETERMINING TRANSDUCER LOCATIONS FOR DELIVERING TUMOR TREATING FIELDS USING A DISCRETIZED MODEL OF A SUBJECT

CROSS-REFERENCE TO RELATED APPLICATIONS

This application claims priority to U.S. Provisional Application No. 63/426,488, filed Nov. 18, 2022, the content of which are incorporated by reference herein in their entirety.

BACKGROUND

Tumor treating fields (TTFields) are low intensity alternating electric fields within the intermediate frequency range (for example, 50 kHz to 1 MHz), which may be used to treat tumors as described in U.S. Pat. No. 7,565,205. TTFields are induced non-invasively into a region of interest by transducers placed on the patient's body and applying alternating current (AC) voltages between the transducers. Conventionally, a first pair of transducers and a second pair of transducers are placed on the subject's body. AC voltage is applied between the first pair of transducers for a first interval of time to generate an electric field with field lines generally running in the front-back direction. Then, AC voltage is applied at the same frequency between the second pair of transducers for a second interval of time to generate an electric field with field lines generally running in the right-left direction. The system then repeats this two-step sequence throughout the treatment.

BRIEF DESCRIPTION OF THE DRAWINGS

FIG. 1 depicts an example method for determining transducer locations for delivering TTFields to a subject.

FIG. 4 depicts an example of displaying a representation of selected transducer locations on a head of the subject.

FIG. 5 depicts an example of displaying a representation of selected transducer locations on a torso of the subject.

FIGS. 6A-6C depict corresponding field magnitude of a segmentation slice processed by the disclosed methods and an example previous method, respectively.

FIGS. 6D-6E depict corresponding accuracy of a visual comparison of field magnitude between the disclosed methods and the previous method.

DESCRIPTION OF EMBODIMENTS

Figure 2A:
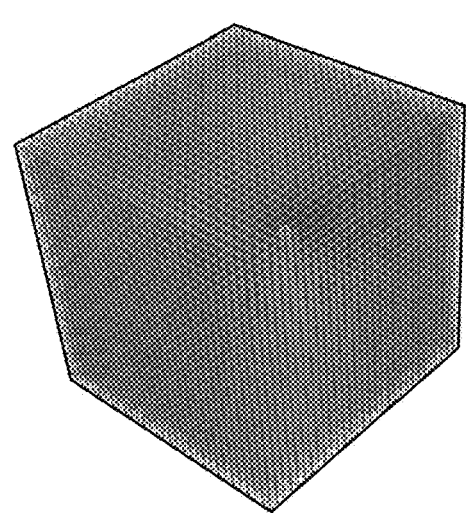
FIG. 2A depicts an example uniform grid of the voxels in a discretized model of a subject.

This application describes exemplary techniques to computationally determine where to place transducers on a subject.

In general, one or more pairs of transducers are positioned on the subject's body and used to alternately apply TTFields to the subject's body. Generally, it is preferred that there are at least two pairs of transducers. Transducers used to apply TTFields to a subject's body often include multiple electrode elements coupled together on a substrate. Determining where to place the transducers on the subject involves using very large data sets and computationally solving complex algorithms. The computations may take a significant amount of time, especially since multiple transducer locations are simulated to determine one or more transducer locations to recommend to achieve an appropriate dosage of the TTFields.

The inventors discovered computational techniques to vastly reduce the computation time needed to solve the complex algorithms and to recommend the one or more transducer locations. The inventive techniques are particularly integrated into a practical application. With the inventive techniques, more transducer locations may be simulated much quicker than previous techniques. With the inventive techniques, simulations for more patients may be performed compared to previous techniques. In addition, a selection of the preferred transducer location(s) may be made from a much greater number of potential transducer locations than is possible in the same amount of time using previous techniques. This may result in improved TTFields treatment efficacy (dosage applied to a region of interest) in the same computational time, since more potential locations are considered in the analysis.

In particular, the inventors discovered computational techniques that include using a discretized model of the subject for solving the complex algorithms, which thereby reduces the computational time. As such, the system described in this disclosure provides a practical application to perform a larger number of iterative optimization processes and/or a same number of iterative optimization processes in less computational time by using a discretized model of the subject to determine and select one or more transducer locations on a subject's body. In some embodiments, the discovered computational techniques lead to the technical advantages of processing a three-dimensional model of a subject based on magnetic resonance imaging (MRI) scans of the subject to efficiently reduce the computational time needed to determine where to place transducers on the subject to deliver corresponding TTFields dosages to the subject.

FIG. 1 depicts an example computer-implemented method 100 for selecting at least one transducer location for delivering TTFields to a subject. The method 100 may be implemented by a computer, the computer including one or more processors and memory accessible by the one or more processors, the memory storing instructions that when executed by the one or more processors cause the computer to perform the steps of the method 100. Modifications, additions, or omissions may be made to method 100. While an order of operations is indicated in FIG. 1 for illustrative purposes, the timing and ordering of such operations may vary where appropriate without negating the purpose and advantages of the examples set forth in detail herein.

The method 100 includes, at step S102, obtaining a three-dimensional (3D) model of the subject. The model includes voxels. Each voxel of the model may be assigned a type of tissue (e.g., bone, organs, fluid, skin, or tumor) and/or an electrical conductivity associated with the type of tissue. As one example, the model of the subject may represent a head of the subject. As an example, the model of the subject may represent a torso of the subject. Other body parts of the subject may be represented in the model of the subject in other embodiments.

The model may be obtained using image data, for example, via a computer identifying the different types of tissue from the image data. The image data may include one or more images of a portion of the subject's body (e.g., X-ray images, MRI images, computerized tomography (CT) images, ultrasound images, or any image providing an internal view of the subject's body). Each medical image may include an outer shape of a portion of the subject and a region corresponding to the region of interest (e.g., tumor) within the subject. The three-dimensional model may be obtained, for example, from computer memory locally or over a network.

At step S104, the method 100 may include computing a cell discretization of the 3D model of the subject to obtain a discretized model. The discretized model of the subject may represent a cell discretization of the model form step S102. As such, the model has voxels and the discretized model has cells, which are based on the voxels in the model. While the 3D model of the subject obtained in step S102 is a discretized version of the actual physical subject, the method in step S104 further discretizes the model from step S102 into a new cell grid. For example, the voxels and their associated quantities and values in the model may be discretized further by discretizing the model into a new cell grid.

In some embodiments, the obtained discretized model may include a uniform cell grid of the voxels or a uniform tensor grid of the voxels in the 3D model of the subject. As an example, to obtain a discretized model with a uniform grid, the model obtained in step S102 may be down-sampled. For example, the model of the subject's body may be down-sampled by using every $n^{th}$ voxel of the model to obtain the discretized model. As an example, down-sampling every $2^{nd}$ voxel (i.e., n=2) of a model having a size of 256×256×256 voxels would result in a discretized model of a size of 128×128×128 voxels. As such for n=2, the number of cells in the discretized model is approximately 12.5% the number of voxels in the model, resulting in a less computationally intensive model thereby saving processing time. As an illustrative example, FIG. 2A depicts an example uniform grid of the voxels in a discretized model of a subject. As can be seen, the uniform grid of the voxels of the model may be evenly distributed in the discretized model of the subject.

Figure 2B:
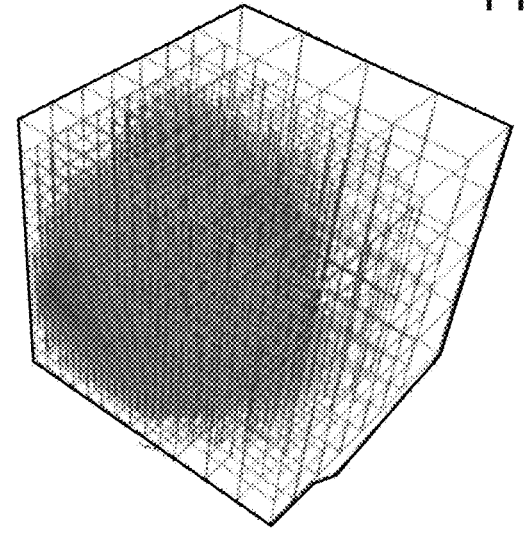
FIG. 2B depicts an example octree grid of the voxels in a discretized model of a subject.
Figure 2C:
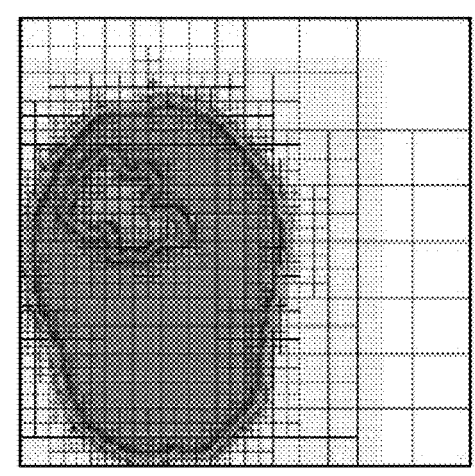
FIG. 2C depicts a slice through the volume in FIG. 2B.

In some embodiments, the obtained discretized model may include a refined octree grid of the voxels in the 3D model of the subject. An octree grid may be a partition of the three-dimensional space of the model by recursively subdividing the space into eight octants. In some embodiments, an octree solver may be used to compute the octree grid and the resulting discretized model. As an illustrative example, FIG. 2B depicts an example octree grid of the voxels in a discretized model of a subject, and FIG. 2C depicts a slice through the volume in FIG. 2B. As can be seen, the octree grid of the voxels of the model may be unevenly distributed in the discretized model of the subject.

In some embodiments, the octree grid may be a refined grid obtained by octree refinement and supported by an underlying uniform grid of the same dimensions as an input segmentation. The octree refinement for the discretized model may be implemented by increasing cell resolution at some locations where a high-resolution grid is needed and decreasing cell resolution at other locations where a high-resolution grid is not needed. For example, an example octree refinement may reduce the number of active cells to achieve more than 50% decrease in cell count. The maximal cell resolution may be an input resolution of the input segmentation.

Quantities for the cells in the discretized model are based on quantities for the voxels in the model from step S102. As one example, the quantity for the cell in the discretized model may be the quantity for the identical voxel in the model. As another example, the quantity for a cell in the discretized model may be the quantity for the closest voxel in the model. As another example, the quantity for a cell in the discretized model may be a calculation of quantities for voxels in the model, where the calculation may be, for example, an average, a maximum, or a minimum of the quantities of the voxels corresponding to some cells in the model.

At step S106, the method 100 may include computing boundary conditions for the discretized model of the subject, wherein the boundary conditions represent one or more transducer locations on the subject. In some embodiments, the boundary conditions may represent the transducer locations as voltage sources on the subject. In some embodiments, the voltage sources may positively charge cover-loops with a set potential positive input voltage values. In some embodiments, the voltage sources may negatively charge cover-loops with a set potential negative input voltage values. In some embodiments, the boundary conditions may represent the transducer locations as current sources on the subject. In some embodiments, the current sources may positively charge the cover-loops by inserting a set current $I_0$. In some embodiments, the current sources may negatively charge cover-loops to remove a set current $I_0$. Setting the desired production current (e.g., =2 [A]) may remove the need for electric field normalization and current computations. In some embodiments, the boundary conditions may represent surface conditions such as a Neumann boundary condition on a surface of the subject.

The term "transducer location" used herein may include more than one location. For example, each "transducer location" may include locations for two pairs of transducers. In such instances, a first pair of the two pairs of transducers has a first transducer and a second transducer located on opposite sides of the subject. Similarly, a second pair of the two pairs of transducers has a third transducer and a fourth transducer located on opposite sides of the subject. Each transducer location may include locations for at least two transducer arrays, with each transducer array including a plurality of electrode elements. The electrode elements on a transducer array may be capacitively coupled or may not be capacitively coupled. The electrode elements on a transducer array may be polymer films or ceramic disks or may take other forms.

At step S108, the method 100 may include computing a matrix A and a vector b. The matrix A may be computed based on the discretized model of the subject. The matrix A may be computed based on one or more types of tissue, tissue conductivity, boundary conditions when using voltage values, and/or other features located in each cell of the discretized model of the subject's body obtained in step S104. Each vector b may be computed based on one or more types of tissue, tissue conductivity, and/or the boundary conditions for each respective transducer location of a plurality of transducer locations. In particular, each vector b may represent the boundary conditions at one of multiple transducer locations within the discretized model of the subject's body. These are the transducer locations from which at least one transducer location will be selected in the method 100. The boundary conditions may represent the transducer locations as voltage sources on the subject, the transducer locations as current sources on the subject, and/or surface conditions such as a Neumann boundary condition on the surface of the subject.

At step S110, the method 100 may include computing a vector φ using the matrix A and the vector b for each transducer location. The vector φ may be computed by solving equation (1):

$$A\phi = b \qquad (1)$$

Each vector φ may represent electrical potentials for the discretized model for each respective transducer location. The vector φ may have a size N×1, where N is the number of active cells in the discretized model. An active cell may be a cell in the discretized model that receives a non-zero potential or that is not air (e.g., background). In some embodiments, computing the vector φ may not be based on background cells (or air cells) of the discretized model. In some embodiments, computing the vector φ may be based on cover-loop cells in the discretized model. The matrix A may be a semi-definite matrix or a positive semi-definite matrix and have a size N×N, where N is a number of active cells in the discretized model.

In some embodiments, equation (1) may be computationally solved based on a computational decomposition of the matrix A. In some embodiments, equation (1) may be computationally solved using at least one of a Cholesky-based direct matrix inversion, an algebraic multigrid (AMG) method, or a conjugate gradient (CG) method. For example, the inverse matrix $A^{-1}$ may be computed using a Cholesky decomposition with the vector φ computed as $A^{-1}*b$, or the vector φ may be computed directly using an AMG method and a CG method.

In some embodiments, a first vector φ and a second vector φ may be computed simultaneously. In some embodiments, the apparatus may include two or more processors, where the first vector φ may be computed using a first processor, and where the second vector φ may be computed using a second processor. In some embodiments, the apparatus may include a processor with two or more cores, where the first vector φ may be computed using a first core, and where the second vector φ may be computed using a second core. In some embodiments, the first vector φ and the second vector φ may be computed in parallel. In some embodiments, the first vector φ may be computed prior to the second vector φ being computed or vice versa.

At step S112, the method 100 may include computing at least one of electric power loss density, current density, or electric field intensity at locations of the discretized model of the subject using the vector φ for each transducer location. These may be the electric power loss density, current density, or electric field intensity at a region of interest (e.g., representing a tumor) within the model. A higher electric power loss density, current density, or electric field intensity in the region of interest may be desired, as this indicates application of a higher dose of TTFields to the region of interest.

As such, the method 100 may be used to compute a dosage of TTFields delivered to the subject. The dosage may be computed based on at least one of the computed electric power loss density, computed current density, or computed electric field intensity of step S112.

At step S114, the method 100 may include computing at least one of local minimum field intensity (LMiFI) or local minimum power density (LMiPD). The LMiFI or LMiPD may represent the minimum dose delivered by the TTFields to a region of interest (e.g., tumor) via the particular transducer layout. The LMiFI and/or the LMiPD may be used to compute an estimated dosage of TTFields that will be delivered to the subject via transducers positioned at the locations corresponding to the vector φ. In some embodiments, the dosage is at least one of the computed LMiFI or computed LMiPD. A higher LMiFI or LMiPD in the region of interest may be desired, as this indicates application of a higher dose of TTFields to the region of interest.

At step S116, the method 100 may include selecting one or more transducer locations for delivering TTFields to the subject. In some embodiments, the one or more transducer locations are selected based on the computed electric power loss density, computed current density, and/or computed electric field intensity from step S112. In particular, the transducer location corresponding to the vector φ associated with the highest computed electric power loss density, the highest computed current density, and/or the highest computed electric field intensity may be selected. In some embodiments, the one or more transducer locations may be selected based on the computed LMiFI or computed LMiPD of step S114. For example, the transducer location corresponding to the vector φ associated with the highest computed LMiFI or LMiPD may be selected.

At step S118, the method 100 may include displaying a representation of the one or more selected transducer locations on a representation of the subject. In some embodiments, step S118 may include displaying at least two selected transducer locations.

One or more processors may execute different algorithms (e.g., solvers) to implement the method 100 to generate a discretized model of the subject for determining locations of one or more transducers to place on the subject and determine corresponding TTFields dosages delivered to the subject. As described above, the method 100 may represent a TTFields tensor solver or algorithm which is implemented based on a discretized model representing the tensor cells over the uniform grid of the voxels in the discretized model. The method 100 may represent a TTFields octree solver or algorithm which is implemented based on a discretized model representing octree cells with a octree grid of the voxels in the discretized model of the subject. Previous technologies or methods may be used to process the model of the subject. The TTFields octree solver and the TTFields tensor solver may be implemented by processing the corresponding discretized models of the subject and reduce a large amount of processing time required by the previous techniques. Some analysis and comparison results are described below.

Figure 3A:
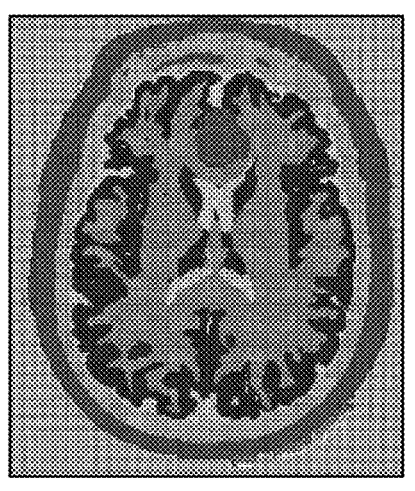
FIG. 3A depicts a visualization of a head segmentation slice on tensor cells.

FIG. 3A depicts a visualization of a head segmentation slice on tensor cells. The head segmentation slice on the tensor cells is based on using a uniform grid of the voxels to obtain the discretized model of the head of the subject.

Figure 3B:
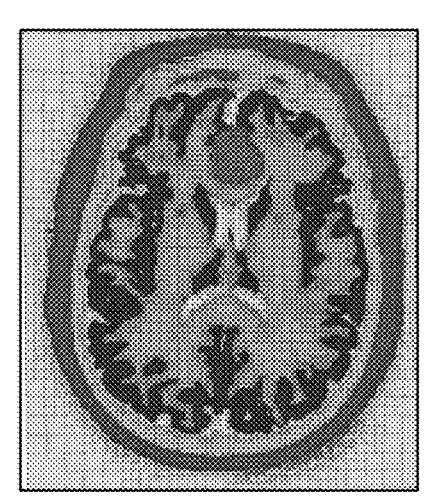
FIG. 3B depicts a visualization of a head segmentation slice on octree cells.

FIG. 3B depicts a visualization of a head segmentation slice on octree cells. The head segmentation slice on the octree cells is based on using an octree grid of the voxels to obtain the discretized model of the head of the subject.

FIG. 4 depicts an example of displaying a representation of selected transducer location on a head of a subject, and FIG. 5 depicts an example of displaying a representation of selected transducer locations on a torso of a subject.

Table 1 provides results of computing the electrical potential (φ) associated with a transducer location on a head of a subject using various methods described above. Table 1 includes example solution computation times based on the TTFields octree solver for a uniform grid, the TTFields tensor solver for an octree grid described above, a first previous solver or method, and a second previous solver or method. In the simulations, the model of the subject includes a plurality of voxels associated with 22,337,705 active cells of the subject and has an image resolution of 1e-05.

TABLE 1

|  | TTFields Tensor Solver | TTFields Tree Solver | Previous Method 1 | Previous Method 2 |
|---|---|---|---|---|
| Solution Computation Times (seconds) | 248.14 | 367.68 | 2767.3 | 1095.9 |

As illustrated in Table 1, the solution computation time using a TTFields tensor solver took 248.14 seconds. The solution computation using a TTFields octree solver took 367.68 seconds. The solution computation by implementing two example previous methods took 2767.3 and 1095.9 seconds, respectively. The solution computation with the TTFields tensor solver was 11.2 times and 4.4 times faster compared to the two previous methods. The solution computation with the TTFields octree solver was 7.5 times and 3.0 times faster compared to the two previous methods. These results indicate good computational time savings using the inventive techniques disclosed herein.

Table 2 provides results of computing the electrical potential ($\phi$) associated with a transducer location on a torso of a subject using various methods described above. Table 2 includes example solution computation times based on the TTFields octree solver for a uniform grid, the TTFields tensor solver for an octree grid described above, a first previous method, and a second previous method.

TABLE 2

|  | TTFields Tensor Solver | TTFields Tree Solver | Previous Method 1 | Previous Method 2 |
|---|---|---|---|---|
| Solution Computation Times (seconds) | 365 | 873.84 | 4321.7 | 2362.3 |

As illustrated in Table 2, the solution computation time using a TTFields tensor solver took 365 seconds. The solution computation using a TTFields octree solver took 873.84 seconds. The solution computation using the two previous methods took 4321.7 and 2362.3 seconds, respectively. The solution computation with a TTFields tensor solver was 11.8 times and 6.5 times faster compared to the two previous methods. The solution computation with a TTFields octree solver was 4.9 times and 2.7 times faster compared to the two previous methods. These results indicate good computational time savings using the inventive techniques disclosed herein.

FIGS. 6A-6C depict corresponding field magnitude of a segmentation slice processed by the TTFields tree solver (FIG. 6A), the TTFields tensor solver (FIG. 6B), and an exemplary previous method ((FIG. 6C). FIG. 6D depicts a visual comparison of field magnitude processed by the TTFields octree solver from FIG. 6A and the exemplary previous method from FIG. 6C. The difference between the two segmentation slices of FIG. 6A and FIG. 6C is depicted in FIG. 6D. FIG. 6E depicts a visual comparison of field magnitude processed by the TTFields tensor solver from FIG. 6B and the exemplary previous method from FIG. 6C. The difference between the two segmentation slices of FIG. 6B and FIG. 6C is depicted in FIG. 6E. As can be seen, the results from the faster inventive computational techniques provides very similar results to those of slower previous techniques.

Exemplary Apparatuses

Figure 7:
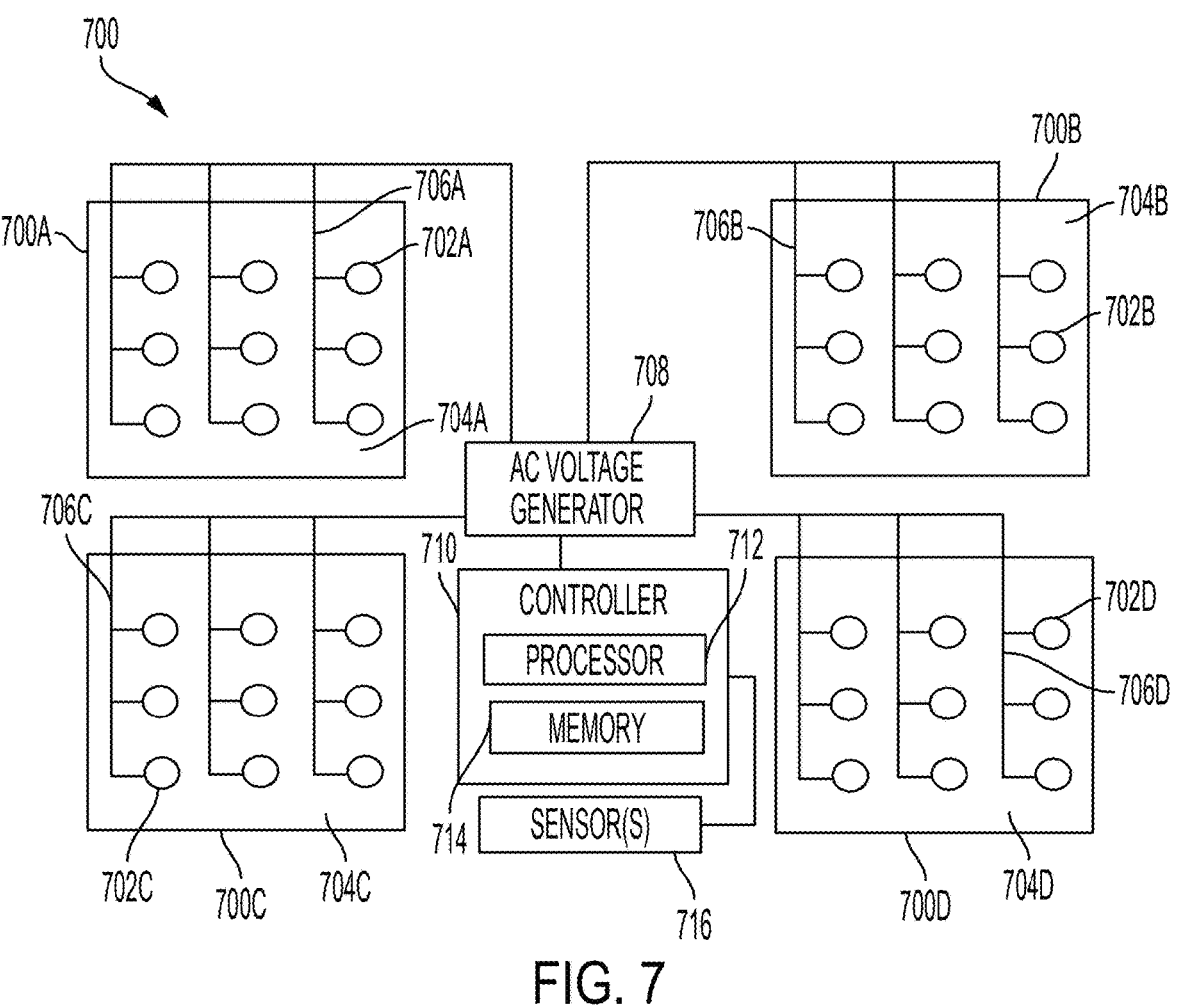
FIG. 7 depicts an example system for delivering TTFields to a subject's body.

FIG. 7 depicts an example apparatus 700 to apply alternating electric fields (e.g., TTFields) to a subject's body. The system may be used for treating a target region of a subject's body with an alternating electric field (e.g., TTFields). As an example, the target region may be in the subject's brain, and an alternating electric field may be delivered to the subject's body via two pairs of transducer arrays positioned on a head of the subject's body (such as, for example, in FIG. 8, which has four transducers 800). As another example, the target region may be in the subject's torso, and an alternating electric field may be delivered to the subject's body via two pairs of transducer arrays positioned on at least one of a thorax, an abdomen, or one or both thighs of the subject's body. Other transducer array placements on the subject's body may be possible.

The example apparatus 700 depicts an example having four transducers (or "transducer arrays") 700A-D. Each transducer 700A-D may include substantially flat electrode elements 702A-D positioned on a substrate 704A-D and electrically and physically connected (e.g., through conductive wiring 706A-D). The substrates 704A-D may include, for example, cloth, foam, flexible plastic, and/or conductive medical gel. Two transducers (e.g., 700A and 700D) may be a first pair of transducers configured to apply an alternating electric field to a target region of the subject's body. The other two transducers (e.g., 700B and 700C) may be a second pair of transducers configured to similarly apply an alternating electric field to the target region.

The transducers 700A-D may be coupled to an AC voltage generator 708 (i.e., AC voltage generator 708), and the system may further include a controller 710 communicatively coupled to the AC voltage generator 708. The controller 710 may include a computer having one or more processors 712 and memory 714 accessible by the one or more processors. The memory 714 may store instructions that when executed by the one or more processors control the AC voltage generator 708 to induce alternating electric fields between pairs of the transducers 700A-D according to one or more voltage waveforms and/or cause the computer to perform one or more methods disclosed herein. The controller 710 may monitor operations performed by the AC voltage generator 708 (e.g., via the processor(s) 712). One or more sensor(s) 716 may be coupled to the controller 710 for providing measurement values or other information to the controller 710.

The electrode elements 702A-D may be capacitively coupled. As an example, the electrode elements 702A-D are ceramic electrode elements coupled to each other via conductive wiring 706A-D. When viewed in a direction perpendicular to its face, the ceramic electrode elements may be circular shaped or non-circular shaped. In other embodiments, the array of electrode elements are not capacitively coupled, and there is no dielectric material (such as ceramic, or high dielectric polymer layer) associated with the electrode elements.

The structure of the transducers 700A-D may take many forms. The transducers may be affixed to the subject's body or attached to or incorporated in clothing covering the subject's body. The transducer may include suitable materials for attaching the transducer to the subject's body. For example, the suitable materials may include cloth, foam, flexible plastic, and/or a conductive medical gel. The transducer may be conductive or non-conductive.

The transducer may include any desired number of electrode elements. Various shapes, sizes, and materials may be used for the electrode elements. Any constructions for implementing the transducer (or electric field generating device) for use with embodiments of the invention may be used as long as they are capable of (a) delivering TTFields to the subject's body and (b) being positioned at the locations specified herein. In certain embodiments, at least one electrode element of the first, the second, the third, or the fourth transducer can include at least one ceramic disk that is adapted to generate an alternating electric field. In non-limiting embodiments, at least one electrode element of the first, the second, the third, or the fourth transducer includes a polymer film that is adapted to generate an alternating field.

Figures 8, 9:
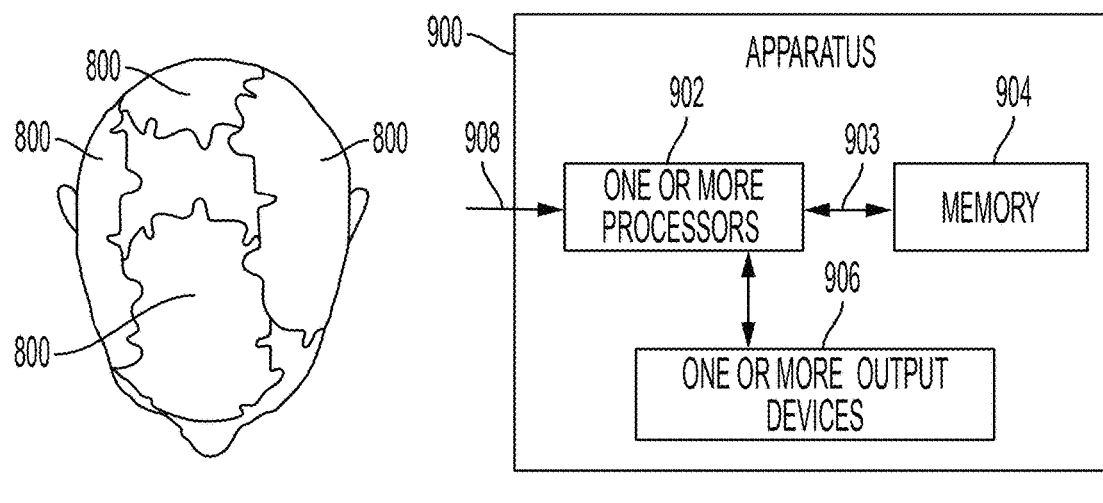
FIG. 8 depicts an example placement of transducers on a subject's head.
FIG. 9 depicts an example apparatus for performing the disclosed methods.

FIG. 9 depicts an example computer apparatus for use with the embodiments herein. As an example, the apparatus 900 may be a computer to implement certain inventive techniques disclosed herein, such as selecting transducer locations for delivering TTFields to a subject. For example, steps S102 to S118 of FIG. 1 may be performed by a computer, such as the apparatus 900. As an example, the apparatus 900 may be used as the controller 710 of FIG. 7, or as a separate computer apparatus located remote from the controller 710. The apparatus 900 may include one or more processors 902, memory 904, one or more input devices, and one or more output devices 906.

As one example, based on input 908, the one or more processors 902 generate control signals to control the voltage generator. As an example, the input 908 may be user input. As an example, the input 908 may be from another computer in communication with the apparatus 900. The input 908 may be received in conjunction with one or more input devices (not shown) of the apparatus 900.

The memory 904 may be accessible by the one or more processors 902 (e.g., via a link 903) so that the one or more processors 902 may read information from and write information to the memory 904. The memory 904 may store instructions that when executed by the one or more processors 902 implement one or more methods of the present disclosure.

The one or more output devices 906 may provide the status of the operation of the invention, such as transducer location selection, voltages being generated, and other operational information. The output device(s) 906 may provide visualization data according to certain embodiments of the invention.

The apparatus 900 may be an apparatus for selecting transducer locations for delivering tumor treating fields to a subject, the apparatus including: one or more processors (such as one or more processors 902); and memory (such as memory 904) accessible by the one or more processors, the memory storing instructions that when executed by the one or more processors, cause the apparatus to perform one or more methods described herein.

The memory 904 may be a non-transitory processor readable medium containing a set of instructions thereon for selecting transducer locations for delivering tumor treating fields to a subject, wherein when executed by a processor (such as processor 902), the instructions cause the processor to perform one or more methods described herein.

ILLUSTRATIVE EMBODIMENTS

The invention includes other illustrative embodiments ("Embodiments") as follows.

Embodiment 1. A computer-implemented method for selecting at least one transducer location for delivering tumor treating fields to a subject, the method comprising: obtaining a three-dimensional model of the subject, the model comprising voxels associated with image data of the subject; computing a discretization of the model to obtain a discretized model; computing boundary conditions for the discretized model, wherein the boundary conditions represent at least transducer locations on the subject; computing a matrix A and a vector b, wherein the matrix A is based on the discretized model, wherein the vector b is based on the boundary conditions for each respective transducer location; computing a vector $\phi$ using the matrix A and the vector b for each transducer location, wherein the vector $\phi$ is computed by computationally solving an equation $A\phi=b$, wherein each vector $\phi$ represents electrical potentials for the discretized model for each respective transducer location; and selecting one or more transducer locations for delivering tumor treating fields to the subject based on the vectors $\phi$.

Illustrative Embodiment 2: The method of Embodiment 1, wherein the discretized model comprises a uniform grid of the voxels in the three-dimensional model of the subject.

Embodiment 3: The method of Embodiment 1, wherein the discretized model comprises an octree grid of the voxels in the three-dimensional model of the subject.

Embodiment 4: The method of Embodiment 1, wherein the boundary conditions represent the transducer locations as voltage sources on the subject.

Embodiment 5: The method of Embodiment 1, wherein the boundary conditions represent the transducer locations as current sources on the subject.

Embodiment 6: The method of Embodiment 1, wherein the boundary conditions further represent a surface of the subject.

Embodiment 7: The method of Embodiment 1, wherein the equation $A\phi=b$ is computationally solved based on a computational decomposition of the matrix A.

Embodiment 8: The method of Embodiment 1, wherein the equation $A\phi=b$ is computationally solved using at least one of a Cholesky-based direct matrix inversion, an algebraic multigrid (AMG) method, or a conjugate gradient (CG) method.

Embodiment 9: The method of Embodiment 1, wherein the matrix A is computed using Cholesky decomposition, and wherein the vector $\phi$ is computed using an algebraic multigrid (AMG) method and a conjugate gradient (CG) method.

Embodiment 10: The method of Embodiment 1, further comprising computing a tumor treating fields dosage of the discretized model of the subject using the vectors $\phi$ for each transducer location, wherein the one or more transducer locations are selected based on the computed tumor treating fields dosages.

Embodiment 11: The method of Embodiment 10, further comprising computing at least one of electric power loss density, current density, or electric field intensity at locations of the discretized model of the subject using the vectors $\phi$ for each transducer location, wherein the tumor treating fields dosage is computed based on the computed electric power loss density, the current density, or the electric field intensity.

Embodiment 12: The method of Embodiment 1, wherein the vector $\phi$ has a size N×1, where N is a number of active cells in the discretized model.

Embodiment 13: The method of Embodiment 1, wherein the matrix A is a semi-definite matrix or a positive semi-definite matrix and has a size N×N, where N is a number of active cells in the discretized model.

Embodiment 14: The method of Embodiment 1, wherein computing the vector $\phi$ is not based on air cells in the discretized model.

Embodiment 15: The method of Embodiment 1, wherein computing the vector $\phi$ is based on cover-loop cells in the discretized model.

Embodiment 16: The method of Embodiment 1, further comprising displaying a representation of a selected transducer location on a representation of the subject.

Embodiment 17: The method of Embodiment 1, further comprising displaying at least two selected transducer locations.

Embodiment 18: The method of Embodiment 1, wherein the model of the subject represents a head of the subject.

Embodiment 19: The method of Embodiment 1, wherein the model of the subject represents a torso of the subject.

Embodiment 20: The method of Embodiment 1, wherein each transducer location comprises locations for two pairs of transducers.

Embodiment 21: The method of Embodiment 20, wherein a first pair of the two pairs of transducers has a first transducer and a second transducer, wherein the first transducer and the second transducer are located on opposite sides of the subject.

Embodiment 22: The method of Embodiment 21, wherein a second pair of the two pairs of transducers has a third transducer and a fourth transducer, wherein the third transducer and the fourth transducer are located on opposite sides of the subject.

Embodiment 23: The method of Embodiment 1, wherein each transducer location comprises locations for at least two transducer arrays, wherein each transducer array comprises a plurality of electrode elements.

Embodiment 24: The method of Embodiment 23, wherein the electrode elements are capacitively coupled.

Embodiment 25: The method of Embodiment 23, wherein the electrode elements are not capacitively coupled.

Embodiment 26: The method of Embodiment 23, wherein the electrode elements comprise polymer films.

Embodiment 27: The method of Embodiment 23, wherein the electrode elements comprise ceramic disks.

Embodiment 28: An apparatus for selecting transducer locations for delivering tumor treating fields to a subject, the apparatus comprising: one or more processors; and a memory accessible by the one or more processors, the memory storing instructions that when executed by the one or more processors, cause the apparatus to: obtain a three-dimensional model of the subject, the model comprising voxels; compute a cell discretization of the model to obtain a discretized model; compute a vector $\phi$ by solving $A\phi=b$ for each of a plurality of transducer locations, A being a matrix based on the discretized model, b being a vector based on the discretized model; compute at least one of electric power loss density, current density, or electric field intensity at locations of the discretized model of the subject using the vectors $\phi$ for each transducer location; and select one or more transducer locations based on the computed electric power loss density, computed current density, or computed electric field intensity.

Embodiment 29: The apparatus of Embodiment 28, wherein the discretized model comprises a uniform grid of the voxels in the three-dimensional model of the subject.

Embodiment 30: The apparatus of Embodiment 28, wherein the discretized model comprises an octree grid of the voxels in the three-dimensional model of the subject.

Embodiment 31: The apparatus of Embodiment 28, wherein the vector $\phi$ is computed for each transducer location based on boundary conditions for each respective transducer location.

Embodiment 32: The apparatus of Embodiment 28, wherein a first vector $\phi$ and a second vector $\phi$ are computed simultaneously.

Embodiment 33: The apparatus of Embodiment 28, wherein the apparatus has two or more processors, wherein a first vector $\phi$ is computed using a first processor, wherein a second vector $\phi$ is computed using a second processor, wherein the first vector $\phi$ and the second vector $\phi$ are computed in parallel.

Embodiment 34: The apparatus of Embodiment 28, wherein a processor of the apparatus has two or more cores, wherein a first vector $\phi$ is computed using a first core of the processor, wherein a second vector $\phi$ is computed using a second core of the processor, wherein the first vector $\phi$ and the second vector $\phi$ are computed in parallel.

Embodiment 35: The apparatus of Embodiment 28, wherein a first vector $\phi$ is computed prior to a second vector $\phi$ being computed.

Embodiment 36: A computer-implemented method for computing a dosage of tumor treating fields delivered to a subject, the method comprising: obtaining a three-dimensional model of the subject, the model comprising voxels; computing a discretization of the model to obtain a discretized model; determining a location on the discretized model of the subject to place a pair of transducers for delivering tumor treating fields; computing boundary conditions for the discretized model, wherein the boundary conditions represent the location of the transducers on the subject; computing a vector $\phi$ by solving $A\phi=b$ for the boundary conditions, A being a matrix based on the discretized model, b being a vector based on the discretized model, the vector $\phi$ representing electrical potentials for the discretized model; computing at least one of electric power loss density, current density, or electric field intensity at locations of the discretized model of the subject using the vector $\phi$; and computing a dosage of tumor treating fields delivered to the subject based on at least one of the computed electric power loss density, computed current density, or computed electric field intensity.

Embodiment 37: The method of Embodiment 36, wherein the dosage is at least one of computed local minimum field intensity or computed minimum field power density.

Embodiments illustrated under any heading or in any portion of the disclosure may be combined with embodiments illustrated under the same or any other heading or other portion of the disclosure unless otherwise indicated herein or otherwise clearly contradicted by context. For example, and without limitation, embodiments described in dependent claim format for a given embodiment (e.g., the given embodiment described in independent claim format) may be combined with other embodiments (described in independent claim format or dependent claim format).

Numerous modifications, alterations, and changes to the described embodiments are possible without departing from the scope of the present invention defined in the claims. It is intended that the present invention not be limited to the described embodiments, but that it has the full scope defined by the language of the following claims, and equivalents thereof.

What is claimed is:

1. A computer-implemented method for selecting at least one transducer location for delivering tumor treating fields to a subject, the method comprising:

obtaining a three-dimensional model of the subject, the model comprising voxels associated with image data of the subject;

computing a discretization of the model to obtain a discretized model;

computing boundary conditions for the discretized model, wherein the boundary conditions represent at least transducer locations on the subject;

computing a matrix A and a vector b, wherein the matrix A is based on the discretized model, wherein the vector b is based on the boundary conditions for each respective transducer location;

computing a vector $\phi$ using the matrix A and the vector b for each transducer location, wherein the vector $\phi$ is computed by computationally solving an equation $A\phi=b$, wherein each vector $\phi$ represents electrical potentials for the discretized model for each respective transducer location; and selecting one or more transducer locations for delivering tumor treating fields to the subject based on the vectors $\phi$.

2. The method of claim 1, wherein the discretized model comprises a uniform grid of the voxels in the three-dimensional model of the subject.

3. The method of claim 1, wherein the discretized model comprises an octree grid of the voxels in the three-dimensional model of the subject.

4. The method of claim 1, wherein the boundary conditions represent the transducer locations as voltage sources on the subject.

5. The method of claim 1, wherein the boundary conditions represent the transducer locations as current sources on the subject.

6. The method of claim 1, wherein the equation $A\phi=b$ is computationally solved based on a Cholesky-based direct matrix inversion of the matrix A.

7. The method of claim 1, wherein the equation $A\phi=b$ is computationally solved using an algebraic multigrid (AMG) method or a conjugate gradient (CG) method.

8. The method of claim 1, further comprising computing a tumor treating fields dosage of the discretized model of the subject using the vectors $\phi$ for each transducer location, wherein the one or more transducer locations are selected based on the computed tumor treating fields dosages.

9. The method of claim 1, wherein computing the vector $\phi$ is not based on air cells in the discretized model.

10. The method of claim 1, wherein computing the vector $\phi$ is based on cover-loop cells in the discretized model.

11. The method of claim 1, further comprising displaying a representation of a selected transducer location on a representation of the subject.

12. The method of claim 1, wherein the model of the subject represents a head of the subject.

13. The method of claim 1, wherein the model of the subject represents a torso of the subject.

14. The method of claim 1, wherein each transducer location comprises locations for at least two transducer arrays, wherein each transducer array comprises a plurality of electrode elements.

15. An apparatus for selecting transducer locations for delivering tumor treating fields to a subject, the apparatus comprising: one or more processors; and memory accessible by the one or more processors, the memory storing instructions that when executed by the one or more processors, cause the apparatus to:

obtain a three-dimensional model of the subject, the model comprising voxels;

compute a cell discretization of the model to obtain a discretized model;

compute a vector $\phi$ by solving $A\phi=b$ for each of a plurality of transducer locations, A being a matrix based on the discretized model, b being a vector based on the discretized model;

compute at least one of electric power loss density, current density, or electric field intensity at locations of the discretized model of the subject using the vectors $\phi$ for each transducer location; and select one or more transducer locations based on the computed electric power loss density, computed current density, or computed electric field intensity.

16. The apparatus of claim 15, wherein the discretized model comprises a uniform grid of the voxels in the three-dimensional model of the subject.

17. The apparatus of claim 15, wherein the discretized model comprises an octree grid of the voxels in the three-dimensional model of the subject.

18. The apparatus of claim 15, wherein the vector $\phi$ is computed for each transducer location based on boundary conditions for each respective transducer location.

19. The apparatus of claim 15, wherein a first vector $\phi$ and a second vector $\phi$ are computed simultaneously.

20. A computer-implemented method for computing a dosage of tumor treating fields delivered to a subject, the method comprising:

obtaining a three-dimensional model of the subject, the model comprising voxels;

computing a discretization of the model to obtain a discretized model;

determining a location on the discretized model of the subject to place a pair of transducers for delivering tumor treating fields;

computing boundary conditions for the discretized model, wherein the boundary conditions represent the location of the transducers on the subject;

computing a vector $\phi$ by solving $A\phi=b$ for the boundary conditions, A being a matrix based on the discretized model, b being a vector based on the discretized model, the vector $\phi$ representing electrical potentials for the discretized model;

computing at least one of electric power loss density, current density, or electric field intensity at locations of the discretized model of the subject using the vector $\phi$; and computing a dosage of tumor treating fields delivered to the subject based on at least one of the computed electric power loss density, computed current density, or computed electric field intensity.

* * * * *